United States Patent [19]

Gobert et al.

[11] Patent Number: 4,696,942
[45] Date of Patent: Sep. 29, 1987

[54] TREATMENT OF MEMORY IMPAIRMENT USING (R)-ALPHA-ETHYL-2-OXO-1-PYRROLIDINEACETAMIDE

[75] Inventors: Jean Gobert; Corneliu Giurgea, both of Brussels; Jean-Pierre Geerts, Leglise; Guy Bodson, Bellefontaine, all of Belgium

[73] Assignee: UCB Societe Anonyme, Brussels, Belgium

[21] Appl. No.: 733,791

[22] Filed: May 14, 1985

[30] Foreign Application Priority Data

May 15, 1984 [GB] United Kingdom ............... 8412358

[51] Int. Cl.$^4$ ............................................. A61K 31/40
[52] U.S. Cl. ................................... 514/424; 548/550
[58] Field of Search ........................ 548/550; 514/424

[56] References Cited

FOREIGN PATENT DOCUMENTS 2081508 12/1971 France .
2368275 5/1978 France .
1309692 3/1973 United Kingdom .

Primary Examiner—Glennon H. Hollrah
Assistant Examiner—D. B. Springer
Attorney, Agent, or Firm—Wenderoth, Lind & Ponack

[57] ABSTRACT (R)-alpha-ethyl-2-oxo-1-pyrrolidineacetamide, its preparation and pharmaceutical compositions containing the same. It can be prepared either by reacting (R)-alpha-ethyl-2-oxo-1-pyrrolidineacetic acid successively with an alkyl haloformate and with ammonia, or, by cyclizing an (R)-2-amino-butanamide of the formula $X-CH_2CH_2-Y-NHCH(C_2H_5)CONH_2$ wherein Y is a $-CH_2-$ radical when X represents a ZOOC— radical and Y is a —CO— radical when X represents a $HalCH_2-$ radical, Z being a $C_1-C_4$ alkyl radical and Hal a halogen atom. This dextrorotatory enantiomer has been found to have significantly higher mnemic activity and lower toxicity than the corresponding racemate.

1 Claim, No Drawings

TREATMENT OF MEMORY IMPAIRMENT USING (R)-ALPHA-ETHYL-2-OXO-1-PYRROLIDINEACETAMIDE

The present invention relates to the novel compound, (R)-alpha-ethyl-2-oxo-1-pyrrolidineacetamide, as well as to processes for the preparation thereof. It also relates to pharmaceutical compositions containing the said compound.

British Pat. No. 1,309,692 describes the compound alpha-ethyl-2-oxo-1-pyrrolidineacetamide (melting point 122° C.) and states that the compounds of this type can be used for therapeutic purposes, for example, for the treatment of motion sickness, hyperkinesia, hypertonia and epilepsy.

Moreover, it also mentions that these compounds can be applied in the field of memory disorders in normal and pathological conditions.

Continuing research work in this field, we have prepared and isolated the dextrorotatory enantiomer of alpha-ethyl-2-oxo-1-pyrrolidineacetamide and have found that this compound differs in a completely unpredictable manner from the known racemic form by
(1) having an about 10 times higher mnemic activity and
(2) having a 3 times lower toxicity.

As a result of this unexpected combination of properties the dextrorotatory enantiomer of alpha-ethyl-2-oxo-1-pyrrolidineacetamide is much more suitable for the treatment of cerebral insufficiencies, memory disorders and difficulties in mental concentration, learning and studying.

Accordingly, the present invention relates to the dextrorotatory enantiomer of alpha-ethyl-2-oxo-1-pyrrolidineacetamide which has the R absolute configuration, the said compound being substantially free from the laevorotatory enantiomer which has the S absolute configuration.

(R)-alpha-ethyl-2-oxo-1-pyrrolidineacetamide according to the present invention cannot be obtained directly from the racemic form by separating the two enantiomers. It can be prepared by one or other of the following processes:

(a) Reacting (R)-alpha-ethyl-2-oxo-1-pyrrolidineacetic acid successively with
(1) an alkyl haloformate of the formula HalCOOZ in which Hal represents a halogen atom and Z an alkyl radical having 1 to 4 carbon atoms, and with (2) ammonia. The alkyl haloformate is preferably ethyl chloroformate.

This reaction is generally carried out in dichloromethane at a temperature between −10° and −60° C.

The (R)-alpha-ethyl-2-oxo-1-pyrrolidineacetic acid, used in this reaction, can be obtained from the racemic (±)-alpha-ethyl-2-oxo-1-pyrrolidineacetic acid by chemical resolution in accordance with methods known per se, for example by forming a salt of this acid with an optically active base, and isolating the salt so formed with (R)-alpha-ethyl-2-oxo-1-pyrrolidineacetic acid by successive crystallizations in an appropriate solvent (for example benzene).

By way of examples of optically active bases which can be used for this resolution there may be mentioned alkaloids such as brucine, quinine, strychnine, quinidine and cinchonidine and amines such as alpha-methylbenzylamine and dehydroabietylamine (cf. S. H. WILEN et al., Tetrahedron, 33, (1977), 2725-2736). Particularly favourable results are obtained by using alpha-methylbenzylamine and dehydroabietylamine.

The racemic (±)-alpha-ethyl-2-oxo-1-pyrrolidineacetic acid used as the starting material can be obtained by saponifying the corresponding alkyl esters, the synthesis of which has been described in British Pat. No. 1,309,692.

(b) Cyclizing an (R)-2-amino-butanamide of the formula

$$X\text{-}CH_2CH_2\text{-}Y\text{-}NHCH(C_2H_5)CONH_2 \quad (A)$$

in which
X represents a ZOOC— or HalCH$_2$— radical, Z being an alkyl radical having 1 to 4 carbon atoms and Hal a halogen atom, preferably chlorine or bromine, and
Y represents a —CH$_2$— or —CO— radical,
with the proviso that Y is a —CH$_2$— radical when X represents a ZOOC— radical, and Y is a —CO— radical when X represents a HalCH$_2$— radical.

The cyclization of the (R)-2-amino-butanamide of formula A is carried out in an inert solvent, such as toluene or dichloromethane, at a temperature of from 0° C. to the boiling point of the solvent. This cyclization is advantageously carried out in the presence of a basic substance as a catalyst. This catalyst is preferably 2-hydroxypyridine when the compound of formula A is an ester (X=ZOOC—), and tetrabutylammonium bromide when the compound of formula A is a halide (X=HalCH$_2$—).

When X represents a ZOOC— radical and Y is a —CH$_2$— radical, the compound of formula A is an alkyl (R)-4[[1-(aminocarbonyl)propyl]amino]-butyrate of the formula ZOOCCH$_2$CH$_2$CH$_2$NHCH(C$_2$H$_5$)CONH$_2$, in which Z has the meaning given above. The latter can be prepared by condensing (R)-2-amino-butanamide with an alkyl 4-halobutyrate of the formula ZOOCCH$_2$CH$_2$CH$_2$Hal, in which Z has the meaning given above and Hal is a halogen atom.

When X represents a HalCH$_2$— radical and Y is thus a —CO— radical, the compound of formula A is (R)-N-[1-(aminocarbonyl)propyl]-4-halobutanamide of the formula HalCH$_2$CH$_2$CH$_2$CONHCH(C$_2$H$_5$)CONH$_2$, in which Hal has the meaning given above. This latter compound can be prepared by condensing (R)-2-amino-butanamide with a 4-halobutyryl halide of the formula HalCH$_2$CH$_2$CH$_2$COHal, in which Hal is a halogen atom.

The reaction between the (R)-2-amino-butanamide on the one hand and the alkyl 4-halobutyrate or 4-halobutyryl halide, on the other hand, is generally carried out in an inert solvent, such as benzene, toluene, dichloromethane or acetone, at a temperature of from −5° to +100° C. and in the presence of an acid acceptor such as a tertiary organic base (for example triethylamine) or an inorganic base (for example potassium carbonate or hydroxide or sodium carbonate or hydroxide).

When X represents a HalCH$_2$— radical and Y a —CO— radical, it is not absolutely necessary to isolate the compound of formula A obtained from the starting materials mentioned above. In fact, the compound of formula A, obtained in situ, can be cyclized directly to the (R)-alpha-ethyl-2-oxo-1-pyrrolidineacetamide according to the present invention (see Example 4 below).

The (R)-2-amino-butanamide used as starting material can be obtained from (R)-2-amino-butyric acid by ammonolysis of the corresponding methyl ester in accordance with the method described by K. FOLKERS et al. in J. Med. Chem. 14, (6), (1977), 484–87.

The following examples are given for the purpose of illustration only.

In these examples, the optical purity of the compounds obtained was verified by calorimetric determination of the differential enthalpies (C. FOUQUEY and J. JACQUES, Tetrahedron, 23, (1967), 4009–19).

EXAMPLE 1

(a) Preparation of the (S)-alpha-methyl-benzylamine salt of (R)-alpha-ethyl-2-oxo-1-pyrrolidineacetic acid 513 g (3 moles) of racemic (±)-alpha-ethyl-2-oxo-1-pyrrolidineacetic acid are suspended in 1.26 liter of anhydrous benzene in a 4 liter flask. To this suspension is added a solution containing 181.5 g (1.5 mole) of (S)-(-)-alphamethyl-benzylamine and 151.8 g (1.5 mole) of triethylamine in 2 liters of anhydrous benzene. The mixture is then heated to reflux temperature until complete dissolution. It is then cooled and allowed to crystallize for a few hours. The crystals are filtered off and washed twice, using 400 ml of benzene. 337 g of the (S)-alpha-methyl-benzylamine salt of (R)-alpha-ethyl-2-oxo-1-pyrrolidineacetic acid are thus obtained. Melting point: 145°–149° C. Yield: 76.9%.

This salt may be purified by heating under reflux in 3 liters of benzene for 4 hours. After cooling and filtration, 297.7 g of the desired salt are thus obtained. Melting point: 149°–152° C. Yield: 68%.

(b) Preparation of (R)-alpha-ethyl-2-oxo-1-pyrrolidineacetic acid 297.7 g of the salt obtained in (a) above are dissolved in 0.6 liter of water. 147.3 g of a 30% sodium hydroxide solution are added slowly, so that the pH of the solution reaches 12.6 and the temperature does not exceed 25° C. The solution is then stirred for a further 20 minutes and the alpha-methyl-benzylamine so liberated is extracted 7 times with 150 ml of benzene.

The aqueous phase is then acidified to a pH of 1.1 by adding 188 ml of 6N hydrochloric acid.

The mixture is stirred for 45 minutes and the acid liberated is extracted 5 times with 200 ml of dichloromethane. The organic phases are combined and dried over magnesium sulfate. After evaporation of the solvent, 170.5 g of (R)-alpha-ethyl-2-oxo-1-pyrrolidineacetic acid are obtained. Melting point: 126° C. [alpha]$_D^{20}$: +27.3° (c=1, acetone). Yield: 98%.

(c) Preparation of (R)-alpha-ethyl-2-oxo-1-pyrrolidineacetamide 17.1 g (0.1 mole) of (R)-alpha-ethyl-2-oxo-1-pyrrolidineacetic acid are suspended in 100 ml of dichloromethane cooled at −13° C. 13.9 ml of triethylamine are then added dropwise. 9.56 ml of ethyl chloroformate are added to the solution so obtained at such a rate that the temperature does not exceed −13° C. The reaction mixture is stirred for half an hour and a stream of ammonia is then passed through it for about two and a half hours.

The reaction mixture is then allowed to return to ambient temperature, and the ammonium salts formed are removed by filtration, and washed with dichloromethane. The solvent is distilled off and the residue is recrystallized from ethyl acetate in the presence of 10 g of molecular sieve (0.3 to 0.4 nm) in powder form.

11.2 G of (R)-alpha-ethyl-2-oxo-1-pyrrolidineacetamide are obtained. Melting point: 115°–117° C. [alpha]$_D^{25}$: +90.7° (c=1, acetone). Yield: 66%.

Analysis for $C_8H_{14}N_2O_2$ in % calculated: C 56.45; H 8.29; N 16.46. found: 56.38; 8.36; 16.43.

The racemic (±)-alpha-ethyl-2-oxo-1-pyrrollidineacetic acid used in the synthesis of (a) has been prepared in the manner described below.

A solution containing 788 g (19.7 moles) of sodium hydroxide in 4.35 liters of water is introduced over 2 hours into a 20 liter flask containing 3.65 kg (18.34 moles) of ethyl (±)-alpha-ethyl-2-oxo-1-pyrrolidineacetate at a temperature not exceeding 60° C. When this addition is complete, the temperature of the mixture is raised to 80° C. and the alcohol formed is distilled off until the temperature of the reaction mixture reaches 100° C.

The reaction mixture is cooled to 0° C. and 1.66 liter (19.80 moles) of 12N hydrochloric acid is added over two and a half hours. The precipitate formed is filtered off, washed with two liters of toluene and recrystallized from isopropyl alcohol. 2.447 kg of racemic (±)-alpha-ethyl-2-oxo-1-pyrrolidineacetic acid, melting at 155°–156° C., are thus obtained. Yield: 78%.

Analysis for $C_8H_{13}NO_3$, in % calculated: C 56.12; H 7.65; N 8.18. found: 55.82; 8.10; 7.97.

EXAMPLE 2

(a) Preparation of ethyl (R)-4-[[1-(aminocarbonyl)propyl]amino]butyrate 143.6 ml (1.035 mole) of triethylamine are added to a suspension of 47.75 g (0.345 mole) of (R)-2-amino-butanamide hydrochloride ([alpha]$_D^{25}$: −26.1°; c=1, methanol) in 400 ml of toluene. The mixture is heated to 80° C. and 67.2 g (0.345 mole) of ethyl 4-bromobutyrate are introduced dropwise.

The reaction mixture is maintained at 80° C. for 10 hours and then filtered hot to remove the triethylamine salts. After evaporation of the filtrate under reduced pressure, 59 g of an oily residue consisting mainly of the monoalkylation product, but containing also a small amount of dialkylated derivative, are obtained.

The product obtained in the crude state has been used as such, without additional purification, in the preparation of (R)-alpha-ethyl-2-oxo-1-pyrrolidineacetamide by cyclization.

(b) Preparation of (R)-alpha-ethyl-2-oxo-1-pyrrolidineacetamide 54 g of the crude product obtained in (a) above are dissolved in 125 ml of toluene in the presence of 2 g of 2-hydroxypyridine. The mixture is kept at 110° C. for 12 hours.

A small amount of insoluble matter is filtered off hot, and the filtrate is then evaporated under reduced pressure.

The residue is purified by chromatography on a column of 1.1 kg of silica (column diameter: 5 cm; eluent: a mixture of ethyl acetate, methanol and concentrated ammonia solution in a proportion by volume of 85:12:3).

The product isolated is recrystallized from 50 ml of ethyl acetate to obtain 17.5 g of (R)-alpha-ethyl-2-oxo-1-pyrrolidineacetamide. Melting point: 117° C. [alpha]$_D^{25}$: +9 0.0° (c=1, acetone). Yield: 41.2%.

EXAMPLE 3

(a) Preparation of (R)-N-[1-(aminocarbonyl)propyl]-4-chlorobutanamide 31.1 g (0.225 mole) of ground potassium carbonate are mixed with 12.47 g (0.09 mole) of (R)-2-aminobutanamide hydrochloride in 160 ml of acetone. The reaction mixture is cooled to 0° C. and a solution of 15.23 g (0.108 mole) of 4-chlorobutyryl chloride in 25 ml of acetone is introduced dropwise. After the addition, the reaction mixture is allowed to return to ambient temperature; the insoluble matter is filtered off and the filtrate evaporated under reduced pressure. The crude residue obtained is stirred in 100 ml of anhydrous ether for 15 minutes at a temperature between 5° and 10° C. The precipitate is filtered off, washed twice with 30 ml of ether, and dried in vacuo to obtain 16 g of (R)-N-[1-(aminocarbonyl)propyl]-4-chlorobutanamide. Melting point: 127°–129° C. [alpha]$_D^{25}$: +22.2° (c=1, methanol). Yield: 86%.

(b) Preparation of (R)-alpha-ethyl-2-oxo-1-pyrrolidineacetamide 6.2 g (0.03 mole) of (R)-N-[1-(aminocarbonyl)-propyl]-4-chlorobutanamide and 0.484 g (0.0015 mole) of tetrabutylammonium bromide are mixed in 42 ml of dichloromethane at 0° C. under a nitrogen atmosphere. 2.02 g (0.036 mole) of potassium hydroxide powder are added over 30 minutes at such a rate that the temperature of the reaction mixture does not exceed +2° C. The mixture is stirred for 15 minutes and then allowed to return to ambient temperature. The insoluble material is filtered off and the filtrate concentrated under reduced pressure. The residue obtained is stirred in 25 ml of carbon tetrachloride for 30 minutes, and then filtered off and dried. The product is recrystallized in 45 ml of ethyl acetate in the presence of 1.7 g of 0,4 nm molecular sieve. The latter is removed by hot filtration to give 3.85 g of (R)-alpha-ethyl-2-oxo-1-pyrrolidineacetamide. Melting point: 116°–118° C. [alpha]$_D^{25}$: +89.8° (c=1, acetone). Yield: 75.4%.

EXAMPLE 4

Preparation of (R)-alpha-ethyl-2-oxo-1-pyrrolidineacetamide

This example illustrates a varient of the process of Example 3, in which the intermediate 4-chlorobutanamide obtained in situ is not isolated.

23 g of potassium hydroxide powder and 9 g of Hyflo-cel are added to a suspension of 13.86 g (0.1 mole) of (R)-2-amino-butanamide hydrochloride in 60 ml of dichloromethane at ambient temperature under nitrogen atmosphere and with vigorous stirring.

The reaction mixture is stirred for 1 hour and the temperature then lowered to about 5° C. 6.52 g (0.02 mole) of tetrabutylammonium bromide are then added, followed over three hours, by a solution of 12.46 ml of 4-chlorobutyryl chloride in 25 ml of dichloromethane. The reaction mixture is stirred at 5° C. for a further hour, and then allowed to return to ambient temperature. Stirring is continued for 23 hours.

The reaction mixture is filtered and the organic phase evaporated under reduced pressure.

The residue is taken up in hot toluene (400% by volume/weight) and the mixture filtered. The solid so obtained is dissolved hot in ethyl acetate (400% by volume/weight), to which 0.4 nm molecular sieve in powder form (32% by weight/weight) is added. This mixture is heated to the reflux temperature and filtered hot. After cooling the filtrate, the desired product crystallizes to give 9.18 g of (R)-alpha-ethyl-2-oxo-1-pyrrolidineacetamide. Melting point: 117° C. [alpha]$_D^{25}$: +89.7° (c=1, acetone). Yield: 54%.

Pharmacological tests

The racemic alpha-ethyl-2-oxo-1-pyrrolidineacetamide (compound A) and the (R)-alpha-ethyl-2-oxo-1-pyrrolidineacetamide (compound B) of the present invention were subjected to pharmacological tests.

I. Mnemic activity

The activity on the mnemic processes is demonstrated by a test employing the antagonism of the amnesia-inducing effect of an electric shock, (S. J. SARA and M. DAVID, Psychopharmacologia, 36, (1974), 59–66).

The principle of the test is as follows:

The reaction of withdrawal of a rat's paw when subjected to an increasing and measured pressure is observed. The pressure at which the withdrawal reaction takes place is referred to as the "reaction threshold". This threshold is expressed by the number of graduations read directly from the scale of the apparatus used (analgesia-meter UGO BASILE Milan) and thus corresponds to the minimum pressure which, applied to the paw of the animals, causes the paw to be withdrawn (learning session). Three measurements are carried out at intervals of 30 minutes.

When tested 24 hours after the end of the learning session, control animals show a natural retention of the previous test, which corresponds to a threshold of the order of 8 to 11 graduations.

The amnesia-inducing effect is produced by applying a trans-temporal supramaximal electric shock (100 mA, 120 Volts, 0.2 sec.) to the rats 15 minutes after the end of the learning session. This amnesia-inducing effect due to the electric shock induces, when measuring the retention 24 hours later, an increase of the avoidance threshold which now corresponds to that of naive animals (which have not undergone a learning session), that is to say a threshold of between 14 and 19 graduations.

For each compound to be tested the minimum active dose (in mg/kg) reestablishing a normal threshold of between 8 to 11 graduations 24 hours after the learning session in animals subjected to electric shock is determined.

The compounds to be tested are administered subcutaneously, as a 10% solution or suspension, to groups of 10 rats (female Wistar rats weighing 150 g) 5 minutes after the end of the learning session. At the same time, a control group of 10 rats is given only a 0.9% aqueous sodium chloride solution.

In this test, the dextrorotatory enantiomer of the invention (compound B) proves to be 10 times more active than the racemate (compound A) in preserving the animals from the amnesia-inducing effect of the electric shock.

| Compound tested | Active dose (mg/kg) |
| --- | --- |
| A | 1.70 |
| B | 0.17 |

II. Toxicity

The following table gives, for compounds A and B, the LD 50 in mg/kg determined on the male mouse and the male rat after intravenous administration:

| Compound tested | LD 50 in mg/kg | |
| --- | --- | --- |
| | mouse | rat |
| A | 1790 | 1500 |
| B | 5603 | 5000 |

As can be seen from this table, the dextrorotatory enantiomer of the invention (compound B) is three times less toxic than the racemate (product A).

The compound of the present invention can be administered either orally in the form of solid or liquid compositions, for example in the form of tablets, pills, dragees, gelatin capsules, solutions or syrups, or parenterally in the form of injectable solutions or suspensions.

Pharmaceutical forms such as solutions or tablets are prepared by conventional pharmaceutical methods. The compound of the invention may be mixed with a solid or liquid non-toxic pharmaceutically acceptable carrier and optionally with a dispersant, a stabilizer and, where necessary, colorants, sweeteners, etc.

Similarly, the solid or liquid pharmaceutical carriers used in these compositions are well known. Solid pharmaceutical excipients for the preparation of tablets or capsules include, for example, starch, talc, calcium carbonate, lactose, sucrose, magnesium stearate, etc. The percentage of active product in the pharmaceutical compositions can vary within very wide limits depending upon the mode of administration and the condition of the patient.

The human posology can vary between 250 mg and 4 g per day. There are given below non-limiting examples of compositions containing the compound of the invention, i.e. a potable solution and a No. 0 gelatin capsule which can be administered orally:

| Ampoule of potable solution | |
| --- | --- |
| compound B | 2.5 g |
| sorbitol (70% in water) | 3.0 g |
| glycerol | 2.5 g |
| glycamil | 0.025 g |
| methylparaben | 0.0135 g |
| propylparaben | 0.0015 g |
| sodium saccharinate | 0.06 g |
| liquorice essence | 0.05 g |
| purified water to make up to | 10 ml |
| Gelatin capsule No. 0 weighing 500 mg | |
| compound B | 500 mg |
| avicel[(x)] | 50 mg |
| magnesium stearate | 5 mg |

[(x)]microcrystalline cellulose

For the treatment in man of memory deficiencies associated with ageing, it has recently been proposed to use a combination of therapies, consisting of administering a drug which enhances brain metabolism, for example piracetam (2-oxo-1-pyrrolidineacetamide), and a choline precursor, such as lecithin or a salt of choline.

According to U.S. Pat. No. 4,385,053, these two substances (piracetam and the choline precursor) co-act synergistically to provide a significant improvement of the memory capabilities in elderly persons suffering from memory deficits and particularly senile dementia of Alzheimer's type.

We have now found a similar synergistic effect between the dextrorotatory enantiomer of the present invention and a choline precursor. Thus, the dextrorotatory enantiomer according to the present invention can also be used advantageously, in combination with a central nervous system cholinergic precursor, for the treatment of memory impairment associated with ageing, senile dementia of Alzheimer's type and the like, in order to obtain a beneficial clinical effect on the learning and memory retention faculties and on the mental faculties in general.

By cholinergic precursor, there is to be understood not only choline or a salt thereof, but also any substance which releases choline in the organism, for example lecithin or phosphatidyl choline. In order to obtain the desired effect, it is essential that said precursor is effective for raising the choline level in the blood and, at the same time, the availability of choline for the synthesis of acetylcholine in the brain.

When the dextrorotatory enantiomer of the present invention is used in conjunction with a cholinergic precursor, it may be administered before or after the administration of the said precursor. Thus, the two products can be administered simultaneously, separately or over a period of time, simultaneous administration being preferred.

Furthermore, the dextrorotatory enantiomer of the present invention can be administered by the same or by a different route from that used for the administration of the cholinergic precursor. Oral administration of both compounds in the currently used pharmaceutical forms (tablets, gelatine capsules, solutions) has been proved to be particularly effective. The dextrorotatory enantiomer of the present invention and the cholinergic precursor can also be administered together in the form of a single dosage unit.

In this particular application, the dextrorotatory enantiomer of the present invention is preferably administered orally in dosages of from 100 mg to 4 grams per day, whereas the cholinergic precursor is preferably administered orally in order to provide the patient with a daily dosage of choline of from 1 to 10 grams. There can be administered, for example, from 2 to 25 grams of phosphatidyl choline per day or from 1 to 30 grams per day of a choline salt. In healthy volunteers, a synergistic effect has been observed by a quantitative analysis of the electroencephalogram after the simultaneous single oral administration of 1.5 grams of the dextrorotatory enantiomer of the present invention and 25 grams of lecithin (18 grams of phosphatidyl choline).

We claim:

1. A method for treating memory impairment in a patient in need thereof which comprises administering to said patient an effective amount of (R)-alpha-ethyl-2-oxo-1-pyrrolidineacetamide.

* * * * *